United States Patent [19]
Tholén et al.

[11] 4,116,041
[45] Sep. 26, 1978

[54] APPARATUS FOR BEARING CAPACITY MEASUREMENT WITH A FALLING WEIGHT DEFLECTOMETER

[75] Inventors: Bengt Olov Tholén; Hans Ivar Hedström, both of Järfälla, Sweden

[73] Assignee: Kuab Konsult och Utveckling AB, Järfälla, Sweden

[21] Appl. No.: 825,077

[22] Filed: Aug. 16, 1977

[30] Foreign Application Priority Data

Aug. 18, 1976 [SE] Sweden .................. 7609211

[51] Int. Cl.$^2$ ............................................. G01N 3/30
[52] U.S. Cl. ........................................... 73/12; 73/662
[58] Field of Search ................................ 73/12, 662

[56] References Cited

U.S. PATENT DOCUMENTS

3,946,598   3/1976   Towne et al. .................. 73/12

FOREIGN PATENT DOCUMENTS

836,023   6/1960   United Kingdom .................. 73/12

*Primary Examiner*—Anthony V. Ciarlante
*Attorney, Agent, or Firm*—Young & Thompson

[57] ABSTRACT

A falling weight deflectometer operates with a falling weight, transmitting shock energy upon its fall to an intermediate weight and to a holder for a pressure plate engaging the ground. Between the falling weight and the intermediate weight is interposed a shock absorber of elastically yieldable material such as shock absorbing rubber, and a corresponding shock absorber is interposed between the intermediate weight and the holder.

7 Claims, 9 Drawing Figures

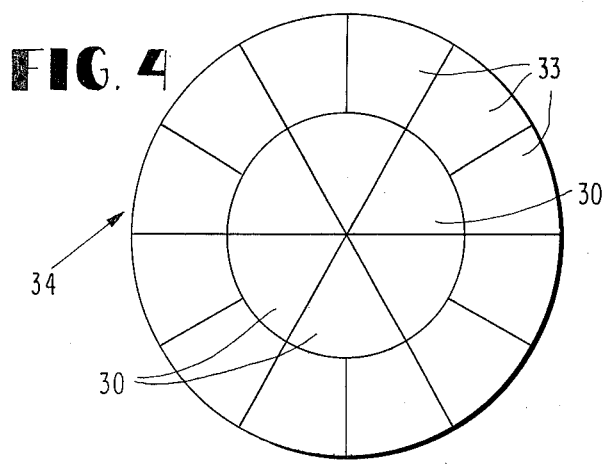
FIG. 4
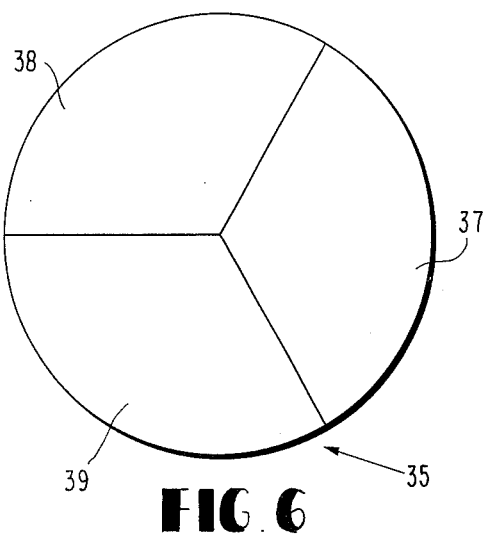
FIG. 6
FIG. 5
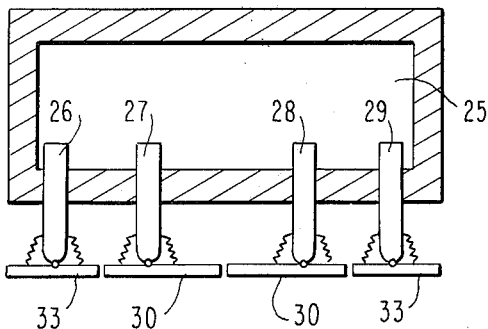
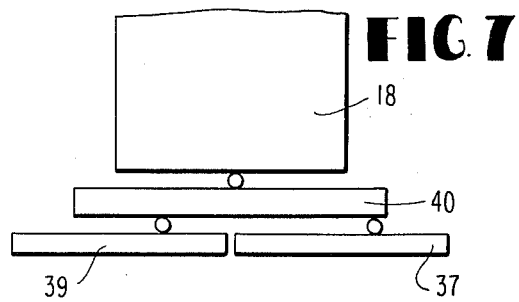
FIG. 7
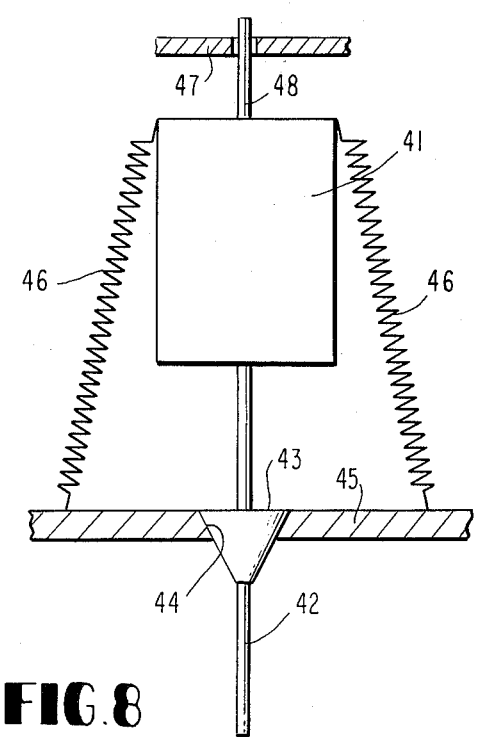
FIG. 8
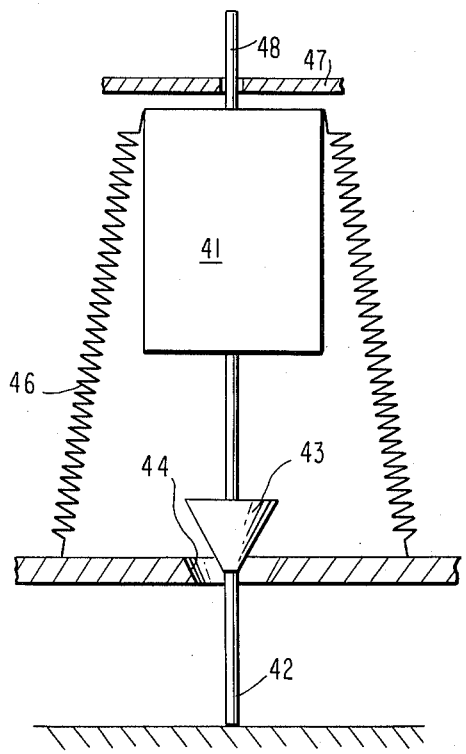
FIG. 9

4,116,041

APPARATUS FOR BEARING CAPACITY MEASUREMENT WITH A FALLING WEIGHT DEFLECTOMETER

The present invention relates to an apparatus for applying a predetermined force on natural stabilized ground material or such material having at least one surface layer. The force is applied by means of a falling weight which is dropped from a predetermined height to strike an intermediate weight which is vertically movable in guides of the frame of the apparatus. The falling weight is also guided for vertical movement in the frame. The shock energy transmitted to the intermediate weight is then transmitted to the ground through a pressure plate connected to the intermediate weight.

The deformation obtained in the ground or other surface to be investigated, is measured in a manner known per se by means of a deflectometer including a seismometer.

The bearing capacity thus measured will give the relation between the force applied and the deformation obtained.

Such measurements are made on roads under construction, or on completed roads, or on air fields in order to check the bearing capacity.

In prior apparatuses of the kind under consideration there is interposed a first shock absorber in the form of a helical spring of steel between the intermediate weight and the pressure plate, and a second shock absorber in the form of a helical spring of steel between the falling weight and the intermediate weight. However, natural resonances will occur in the helical springs resulting in a damping of the force from the falling weight, and mainly due to these natural resonances the actual curve for the variations of the force applied to the ground as a function of time, will differ considerably from the theoretical curve.

The object of the invention is therefore to provide an apparatus of the kind under consideration which will result in an actual measured force curve which has an increased conformity with the theoretical force curve.

More specifically the apparatus according to the invention is an apparatus for bearing capacity measurements with a falling weight deflectometer, comprising a frame structure for guiding a vertically movable intermediate weight of a predetermined mass and adapted to be supported by a pressure plate adapted to rest on the material to be measured such as a road, completed or in construction stage, a first shock absorber being interposed between the intermediate weight and the pressure plate, a falling weight being movable vertically along guides of the frame structure under the influence of gravity from a predetermined height to strike the intermediate weight through the medium of a second shock absorber.

The improvement desired is obtained in such an apparatus which according to the invention is characterized in that one of the two shock absorbers, preferably both, is comprised of a body of elastically yieldable material such as shock absorbing rubber. The elastically yieldable material shall have a low specific weight and a high shock absorbing capacity in relation to conventional helical springs of steel.

The simple means suggested by the invention will result in a substantial improvement as to the desire to create force pulses of desired frequency and amplitude, which are substantially independent of the loaded surface.

Another object of the invention is also to eliminate transverse movements of the movable parts of the apparatus, because such transverse movements will reduce the measuring accuracy.

These and other objects and advantages of the invention will appear from the following description of two embodiments of the invention.

FIG. 4 is an end view of the pressure plate comprising a number of individually movable sub-plates.

FIG. 5 is a diagrammatic sectional view of a device for actuating the sub-plates in FIG. 4.

FIG. 6 is a bottom view of another embodiment of the pressure plate.

FIG. 7 is a partial elevational view of the pressure plate in FIG. 6.

FIGS. 8 and 9 are diagrammatic views of the measuring instrument with its rod for sensing the deformation.

Figure 1:
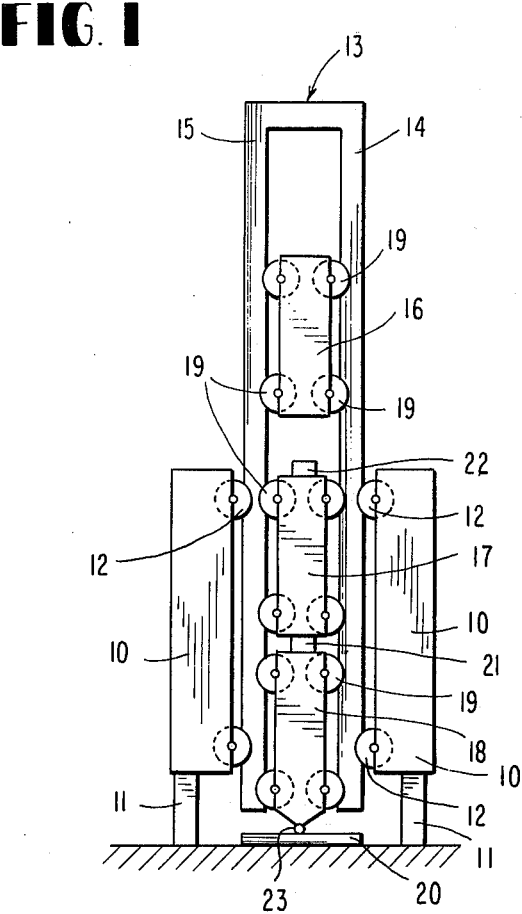
FIG. 1 is a diagrammatic view of an embodiment of the apparatus according to the invention.

In FIG. 1, the apparatus comprises a frame structure including a stationary frame 10 which may be carried by a trailer vehicle (not shown) and has a number of vertically adjustable supporting feet 11. Before measuring, the supporting feet 11 are lowered to the ground and adjusted so that the wheels of the trailer become unloaded and the apparatus is positioned substantially at right angles to the ground or road.

The stationary frame 10 has guide rollers 12 for guiding a movable frame 13 which has two guide pieces or cylindrical shafts 14, 15 engaging the guide rollers 12.

Between the guide pieces 14, 15 are provided a falling weight 16, an intermediate weight 17 and a pressure plate holder 18, which all are vertically movable and guided along the guide pieces 14,15 by means of rollers 19.

On top of the holder 18 or other member connected to the pressure plate 20, is a first shock absorber 21 in the form of a body of shock absorbing rubber to transmit shock energy from the intermediate weight to the pressure plate and the ground.

On top of the intermediate weight is a second shock absorber 22 of shock absorbing rubber for transmitting shock energy from the falling weight to the intermediate weight. The shock absorbing rubber used may be of the kind which is sold in Sweden under the registered trade mark NOVIBRA.

All rollers 12,19 are adjustable to obtain a desired minimum clearance or play in the respective guide path.

When the supporting feet have been lowered to support the apparatus, as mentioned above, the movable frame 14 is lowered so that the pressure plate 20 will rest on the ground. The pressure plate 20 has a pivotal joint 23 for connection with the holder 18, so that the pressure plate will adjust itself to any inclination of the ground.

Within the holder 18 is provided the necessary measuring instrument, normally a seismometer. This instrument is supported by a vertical pressure rod extending through an opening in the pressure plate to engage the ground, in a manner known per se.

The falling weight 16 is raised to a predetermined height, in a manner known per se, by means of a pressure liquid cylinder (not shown) provided on the frame 13. Thereafter, the falling weight is dropped and the shock force obtained is transmitted via the rubber shock absorbers 19, 21, intermediate weight 17 and the holder 18 to the pressure plate. A certain deformation of the ground is obtained and is registered by means of the measuring instruments.

When measurements are made on completed roads or roads in the construction stage, the amplitude and time history of the force pulse may be chosen in order to give the road a deformation which as far as possible simulates the deflection caused by a 50,000 Newtons lorry wheel passing at normal speed. The deflection of the road surface is measured in the centre of the loaded area, and in another point, usually 450 mm from the loading centre.

The measuring time at one test point is by standard procedure about 30 seconds, and on gravel roads and other very low trafficated roads, where another procedure is used, about 40 seconds. If, for example, a distance of 100 meters between the test points is used, the capacity of measuring is about 6 to 7 kilometers per hour.

Figure 2:
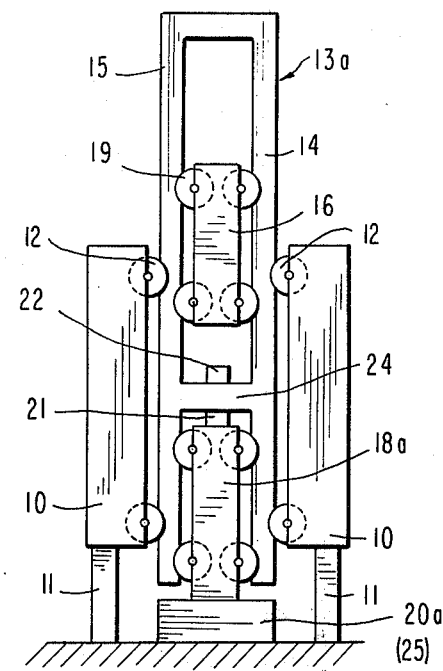
FIG. 2 is a diagrammatic view of a second and preferred embodiment of the apparatus.

FIG. 2 shows a modified and preferred embodiment of the apparatus which differs from that in FIG. 1 in that the intermediate weight 17 in FIG. 1 is substituted by a cross-plate or cross-bar 24 between the side pieces 14, 15 of the movable frame 13a. This cross-bar 24 is resting on the first shock absorber 21 on top of the holder 18a, and on the cross-bar is mounted the second shock absorber 22 provided to receive the falling weight 16. Accordingly, the intermediate weight in this preferred embodiment is comprised of the movable frame 13a.

The apparatus in FIG. 2 can be made considerably shorter in height because it only requires shorter guides than in the apparatus in FIG. 1. The weight of the apparatus in FIG. 2 will accordingly have a lesser weight which is further reduced because the intermediate weight 17 in FIG. 1 has been omitted. The falling height for the falling weight 16 may be measured easier from the ground surface.

The movable guiding frame 13a will rest on the holder 18a, and the falling height may be readily measured between the falling weight 16 and the cross-bar 24 of the frame 13a when the holder 18a with the pressure plate 20a is resting on the ground.

Figure 3:
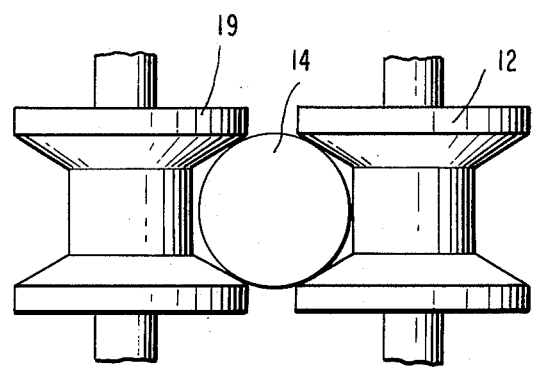
FIG. 3 is a partial top view of the apparatus in FIG. 2.

FIG. 3 shows the rollers 12, 19 in engagement with the vertical guide shaft 14 to guide the falling weight, intermediate weight and the holder for the pressure plate. By means of these rollers the guiding of the movable parts can be adjusted so that the play at right angles to the direction of loading is practically nil, whereas it will permit easy movement in the direction of load independent of transverse forces, temperature variations, dirt and wear. The stiffness of the guiding device described will result in that the mass of the apparatus may effectively by utilized to counteract transverse movements of the pressure plate. Due to the design of the apparatus disclosed, the holder for the pressure plate, the intermediate weight and the falling weight may pass the attachments to the stationary frame 10 so that the pressure plate may also be lowered into cavities in the ground.

The pivotal connection 23 between the pressure plate 20 and holder 18 in FIG. 1 is of known design and the pressure plate is a stiff plate.

However, according to the invention, the pressure plate may be of the design diagrammatically indicated at 20a in FIG. 2 and illustrated more in detail in FIGS. 4 and 5.

To the holder 18a in FIG. 5 is rigidly secured a liquid pressure chamber 25 as shown in FIG. 5. In the bottom 26 of the chamber are journalled a number of pistons or plungers 26, 27, 28, 29 which are vertically movable and have their upper ends located in the chamber and are subjected to the pressure therein. The lower end of each plunger is pivotally connected to a sub-plate 30, 33, and these sub-plates form together the total pressure plate 34 shown in FIG. 4. Each sub-plate will accordingly adjust itself to the local level and inclination of the ground, and the load on the respective sub-plate will be substantially independent of the local shape of the surface of the ground or road subjected to the load from the respective sub-plate, and will also be substantially independent of the deformation of the surface of the ground.

When a vertical load is applied on the chamber 25, this load is through the medium of the pressure oil in the chamber distributed to the sub-plates through the top surfaces of the plunges. The total pressure plate 34 will accordingly function as a load distributing plate adapting itself to irregularities of the surface of the ground.

In FIGS. 6 and 7 is shown a simplified embodiment of a load distributing pressure plate 35, which is comprised of a number of sector-shaped sub-plates 37, 38, 39, which are pivotally attached to a main plate 40 pivotally connected to the holder 18. The sub-plates are accordingly adjustable independent of each other in order to distribute the force on the holder to the respective sub-plate. A greater number of sub-plates than shown may be used.

FIGS. 8 and 9 illustrate diagrammatically the principle for automatic adjustment of the measuring in a correct position in relation to the pressure plate. The instrument 41 has a pressure rod 42 which in its measuring position engages the ground surface and follows the deformation of the ground. The rod 42 is provided with a conical centering body 43 which upon transportation of the apparatus is seated in a conical opening 44 in a plate 45 which may be secured to the pressure plate. The instrument and its rod 42 is biased towards the ground by means of springs 46. On top of the instrument is a further coaxial rod 48 guided in an opening in a guide plate 47 secured to the holder.

When lowering the instrument 41 to measuring position, in which the rod 42 engages the ground as illustrated in FIG. 9, the conical body 43 is released from the seat 44 and the rod is located in the opening of the seat 44. As will be seen from FIG. 9, the minimum diameter of the conical opening or seat 44 is several times greater than the outer diameter of the rod 42 so that the instrument is safely disengaged from the seat 44.

What we claim is:

1. An apparatus for bearing capacity measurement with a falling weight deflectometer comprising a frame structure for guiding a vertically movable intermediate weight of a predetermined mass and adapted to be supported by a pressure plate adapted to rest on the material to be measured such as the ground, a road, completed or in construction stage, a first shock absorber being interposed between the intermediate weight and the pressure plate, a falling weight being movable vertically along guides of the frame structure under the influence of gravity from a predetermined height to strike the intermediate weight through the medium of a second shock absorber, characterized in that one of the two shock absorbers is comprised of a body of elastically yieldable material such as shock absorbing rubber.

2. An apparatus according to claim 1, in which the two shock absorbers are both of elastically yieldable material such as shock absorbing rubber.

3. An apparatus according to claim 1 in which the elastically yieldable material has a low specific weight and a high shock absorbing capacity in relation to conventional steel helical springs.

4. Apparatus according to claim 1 in which the frame of the apparatus is supported by adjustable support feet which are adjustable so that the path of movement of the falling weight will be substantially perpendicular to the surface of the material to be measured.

5. Apparatus according to claim 1 in which the intermediate weight comprises a sub-frame which is vertically movable in the frame of the apparatus and is provided to constitute the intermediate weight due to the fact that the sub-frame rests on the first shock absorber which is provided on top of a holder carrying the pressure plate and being guided in the sub-frame, and the falling weight is guided by the sub-frame and is adapted to transmit the shock energy to the sub-frame through the second shock absorber.

6. An apparatus according to claim 1 characterized in that the pressure plate is comprised of a number of sub-plates, and that a number of vertically movable holders pivotally support each one of said sub-plates and are provided each with a piston which extends into a liquid pressure chamber which is common for all pistons, said chamber being axially movable in the frame and supporting said first shock absorber.

7. Apparatus according to claim 1 including a seismometer which has a substantially vertical pressure rod adapted to engage the ground surface before starting the measurement, said pressure rod being guided in an opening in a member supported by the frame so as to take a correct position against the ground, characterized in that the opening is formed as a conical seat for receiving a conical centering body mounted on the pressure rod, and that the minimum internal diameter of the conical seat is several times greater than the outer diameter of the pressure rod so that the rod will take a correct position in its resting position with the conical body engaging the seat, whereas the rod upon measurement will have a satisfactory freedom of movement radially in the conical opening forming the seat.

* * * * *